United States Patent

Takeoka et al.

Patent Number: 6,139,852
Date of Patent: *Oct. 31, 2000

[54] EXTRACT COMPOSITION AS HAIR GROWTH PHASE EXTENDER

[75] Inventors: Eriko Takeoka; Chika Hamada; Jun Suzuki; Yosuke Nakazawa; Tsutomu Souma; Masashi Ogou; Masahiro Tajima, all of Yokohama, Japan

[73] Assignee: Shiseido Company, Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/047,447

[22] Filed: Mar. 25, 1998

[30] Foreign Application Priority Data

Mar. 26, 1997 [JP] Japan .................................. 9-091533
Sep. 22, 1997 [JP] Japan .................................. 9-275261

[51] Int. Cl.⁷ ................................ A61K 7/00; A61K 7/06
[52] U.S. Cl. ..................... 424/401; 424/70.1; 424/195.1; 514/880
[58] Field of Search ................................ 424/70.1, 195.1, 424/401; 514/880

[56] References Cited

FOREIGN PATENT DOCUMENTS

| | | |
|---|---|---|
| 0 304 603 | 3/1989 | European Pat. Off. . |
| 0 309 086 | 3/1989 | European Pat. Off. . |
| 569 667 A2 | 11/1993 | European Pat. Off. . |
| 4 207 636 A1 | 9/1993 | Germany . |
| 2 033 146 C1 | 4/1995 | Russian Federation . |
| 2 218 334 | 5/1989 | United Kingdom . |

OTHER PUBLICATIONS

Rogers et al., Journal of Investigative Dermatology, Cultivation of Murine Hair Follicles as Organoids in a Collagen Matrix, (1987), pp 369–379.

*Primary Examiner*—Thurman K. Page
*Assistant Examiner*—Brian K. Seidleck
*Attorney, Agent, or Firm*—Foley & Lardner

[57] ABSTRACT

A hair growth phase extender containing, as an effective ingredient, at least one compound selected from the group consisting of unsaturated fatty acid and/or its derivatives, especially an unsaturated fatty acid having the formula:

$$C_nH_mO_2$$

where n is 12 to 28 and m is n+1 to 2n−2; or containing, as an effective ingredient, an extract of a plant belonging to the Coriandrum.

4 Claims, No Drawings

EXTRACT COMPOSITION AS HAIR GROWTH PHASE EXTENDER

BACKGROUND OF THE INVENTION

1. Field of the Invention

The present invention relates to a hair growth phase extender composition. More specifically, it relates to a hair growth phase extender composition which maintains or extends the growth phase in the hair cycle by promoting hair growth.

2. Description of the Related Art

In modern day society, called a high aging society, high stress society, the opportunities for the hair on the head to be exposed to the risk of loss have become increasingly prevalent due to various factors.

To deal with this, various attempts have been made to provide more superior "hair tonics".

The main effects which hair tonics have on the hair are (1) an effect of inducing hair formation (effect of promoting hair formation and effect of inducing growth phase), (2) an effect of thickening hair, (3) an effect of extending the growth phase of hair, (4) an effect of inhibiting 5α-reductase, (5) an effect of promoting blood circulation, (6) a sterilizing effect, (7) an anti-dandruff effect, (8) a moisturizing effect, (9) an anti-oxidation effect, and other effects.

However, despite the various attempts made in this way, conventional hair tonics have not necessarily sufficiently acted to prevent hair loss, promote hair formation, etc. This is believed to be because there are probably various reasons for hair loss and the mechanism of hair formation is extremely complicated. The "hair tonics" provided up to now have been developed focusing on the relatively general concept of hair loss, in other words, the phenomenon of "hair loss". Not that many have been developed delving into the mechanism of the same.

The major reason is undeniably due in part to the fact that no sufficient method of evaluating hair growth drugs has been proposed enabling simple evaluating of the effect of hair formation focusing on this mechanism. In particular, it is difficult to establish a method of evaluating hair growth drugs which evaluates the (3) effect of extension of the hair growth phase. As a result, the hair tonics provided up to now have mostly focused on the above (1) effect of inducement of hair formation which promotes hair by inducing hair in the growth phase of the hair cycle and the (4) effect of blocking 5α-reductase.

SUMMARY OF THE INVENTION

Therefore, the present inventors aimed at establishing a simple in vitro method of evaluating a hair growth agent for evaluating the effect (3) of extension of the hair growth phase and using the method of evaluating the hair growth agent to find a hair growth phase extender composition containing an ingredient having the above effect (3) of extension of the hair growth phase as an effective ingredient.

Accordingly, the object of the present invention are to obviate the above-mentioned problems in the prior art and to provide an active ingredient having the above effect (3) of extension of the hair growth phase and to provide a hair growth phase extender composition containing the same as an effective ingredient.

In accordance with the present invention, there is provided a hair phase extender composition comprising at least one compound selected from the group consisting of unsaturated fatty acids and the derivatives thereof, as an effective ingredient, and a carrier therefor.

In accordance with the present invention, there is also provided a high growth phase extender composition comprising an abstract of a plant belonging to the Coriandrum as an effective ingredient and a carrier therefor.

DESCRIPTION OF THE PREFERRED EMBODIMENTS

The present inventors engaged in intensive studies on an ingredient having the above effect (3) of extension of the hair growth phase in various substances using the method of evaluating a hair growth agent found by the present inventors and found that the desired effect of extension of the hair growth phase was observed in unsaturated fatty acids and/or their derivatives and also in an extract of plants belonging to the Coriandrum such as coriander.

Thus, according to the first aspect of the present invention, a hair growth phase extender composition containing an unsaturated fatty acid and/or its derivative as an effective ingredient is provided.

The unsaturated fatty acids usable in the present invention are those having the formula:

$$C_nH_mO_2$$

where n is 12 to 28 and m is n+1 to 2n−2.

Further, of these unsaturated fatty acids, it is preferable to select an unsaturated fatty acid having a cis-form double bond.

Examples of such an unsaturated fatty acid satisfying these conditions are a dodecenoic acid, tridecenoic acid, heptadecenoic acid, petroselinic acid, palmitoleic acid, oleic acid, vaccenic acid, linolic acid, α-linoleic acid, γ-linoleic acid, eicosenoic acid, eicosatrienoic acid, erucic acid (cis-13-docosenoic acid), docosadienoic acid, docosatrienoic acid, docosatetraenoic acid, docosapentaenoic acid, arachidonic acid, nervonic acid, and docosahexaenoic acid. These unsaturated acids may be used alone or in any mixture thereof. Of these unsaturated fatty acids, the particularly preferable unsaturated fatty acid is petroselinic acid, docosahexaenoic acid, or oleic acid.

As explained above, in the present invention, the "hair growth phase extender" is a hair related agent which is formulated having as an effective ingredient an ingredient having an effect of extending the growth phase of the hair by maintaining or promoting the schizogenesis action of the follicular epithelial cells or the growth action of the hair roots by the method of evaluating a hair growth agent explained later, particularly takes note of the effect (3) of extension of the hair growth phase, that is, has the characteristic of a so-called "individual effect hair tonic".

This "hair growth phase extender" is, for example, an agent particularly effective against alopecia derived from the facts that the proliferation of follicular epithelial cells near the hair roots is slow, whereby the growth phase becomes shorter and the proportion of the quiescent phase hair becomes relatively greater than the growth phase hair. Further, by combining and using hair tonics having other individual effects, it is possible to raise the overall synergistic effect in a broader range of alopecia. That is, this "hair growth phase extender" has a concept encompassing the effects of (1) to (9) explained above and has applications different from general hair tonic applications.

The hair growth phase extender according to the first aspect of the present invention contains an unsaturated fatty acid and/or its derivative as an effective ingredient as explained above.

The unsaturated fatty acids capable of using, as the effective ingredient of the hair growth phase extender according to this aspect of the present invention is not particularly limited so long as safety to the human body is ensured, but unsaturated fatty acids having from 12 to 28 carbon atoms and having a cis-form double bond is preferable. Specific examples are dodecenoic acid, tridecenoic acid, heptadecenoic acid, petroselinic acid (cis-6-octadecenoic acid), palmitoleic acid (cis-9-hexadecenoic acid), oleic acid, vaccenic acid, linolic acid, α-linoleic acid, γ-linoleic acid, eicosenoic acid, eicosatrienoic acid, erucic acid (cis-13-docosenoic acid), docosadienoic acid, docosatrienoic acid, docosatetraenoic acid, docosapentaenoic acid, arachidonic acid, nervonic acid (cis-15-tetracosenoic acid), or docosahexaenoic acid.

Among these unsaturated fatty acids, it is particularly preferable to select petroselinic acid, docosahexaenoic acid, and/or oleic acid.

Note that, as the material of the unsaturated fatty acids, it is further preferable to select a plant, for example, coriander, comfrey, and other unsaturated fatty acids as the effective ingredient of the hair growth phase extender of the present invention.

Further, as the effective ingredient of the hair growth phase extender according to the present invention, derivatives of these unsaturated fatty acids can be used.

Specific examples of the derivatives are unsaturated fatty acid monoglycerides, unsaturated fatty acid diglycerides, unsaturated fatty acid triglycerides, pharmaceutically acceptable unsaturated fatty acid salts, unsaturated fatty acid esters, unsaturated fatty acid amides, unsaturated fatty acid dibasic acids, or pharmaceutically acceptable salts thereof.

These unsaturated fatty acids or their derivatives may be produced by normally known methods. Further, commercially available products are, of course, usable in the present invention.

These fatty acids and their derivatives have a strong action in proliferating follicular epithelial cells and action in growth of hair roots. It is possible to use them alone or in any combination thereof for the effective ingredient of the hair growth phase extender according to the present invention.

The amount of the above unsaturated fatty acid and/or its derivative formulated in the hair growth phase extender composition of the present invention may be suitably selected, depending upon the specific form of the hair growth phase extender composition of the present invention. It is not particularly limited, but preferably is from $1.0 \times 10^{-9}\%$ by weight to 20.0% by weight, more preferably from 0.01% by weight to 10.0% by weight, based upon the total weight of the composition.

When the amount is less than $1.0 \times 10^{-9}\%$ by weight, the desired effect of the present invention, that is, the effect of extension of the hair growth phase, based on the action of proliferation of the follicular epithelial cells, is not sufficiently exhibited, and therefore, is not preferable. Even if the amount is more than 20.0% by weight, not only can no increase in effect commensurate with the increase in the amount be expected, but also there is a remarkable trend toward causing problems in the preparation of the composition.

In this way, the hair growth phase extender composition according to the present invention containing the above unsaturated fatty acid or its derivative as an effective ingredient has an effect of extending the hair growth phase, based on the superior action of proliferating the follicular epithelial cells. As explained above, for example, the hair growth phase extender composition according to the present invention is an agent particularly effective against alopecia derived from the facts that the proliferation of follicular epithelial cells near the hair roots is slow, whereby the growth phase becomes shorter, and the proportion of the quiescent phase hair becomes relatively greater than the growth phase hair. Further, by combining and using hair tonics having other individual effects, it is possible to raise the synergistic effect in specific alopecia.

The means for specifying the action in maintaining or extending the growth phase in a hair cycle, the inherent action in the desired effect of the hair growth phase extender of the present invention, that is, the effect of extending the hair growth phase, is not particularly limited so long as the specified method is suitable for specifying the action. For example, a specified in vitro method or a specified in vivo method may be used, but considering the convenience and effectiveness, it is preferable to use a specified in vitro method.

The hair growth phase extender according to the second aspect of the present invention contains an extract of plants belonging to the Coriandrum of the Umbelliferae as an effective ingredient.

Specific examples of the plants belonging to the Coriandrum are *Coriandrum sativum L.*, generally known as coriander, but so long as the extract has the action of extending the growth phase in the hair cycle, it may belong to varieties, subspecies, and the like as well.

Further, the extracts of plants belonging to the Coriandrum may be obtained advantageously from the adult form or immature fruit of these plants, but can also be extracted from the mature fruit (note: the portions serving as materials for these extracts are also referred to overall as "plants belonging to the Coriandrum").

When extracting the extracts of plants belonging to the Coriandrum, any methods generally used when extracting plant-derived extracts can be used.

That is, a plant belonging to the Coriandrum may be used for solvent extraction in the fresh state or, if desired, dried, then used as it is or pulverized. The solvent used for extraction may be any conventional solvent generally usable when extracting the ingredients of a plant from the plant and is not particularly limited. For example, hot water; lower alcohols such as methanol, ethanol, isopropanol, n-heptanol; polyols such as propylene glycol, 1,3-butylene glycol, aqueous alcohols thereof; hydrocarbon solvents, etc. such as n-hexane, toluene may be mentioned, but lower alcohols such as methanol, ethanol, are preferably used as the extraction solvents. When these lower alcohols are used as extraction solvents, the resultant extracts may be directly included, as effective ingredients, in the hair growth period extender composition of the present invention as they are, but it is also possible to first distill the extraction solvents off and then formulate them into the composition after drying, if desired.

The extracts of plants belonging to the Coriandrum obtained in this way are confirmed to contain essential oils such as at least d-linalol, pinene, fatty oils such as petroselinic acid, oil acid (or oleic acid), and proteins, sugar, long chain aliphatic aldehydes, etc.

It is not clear if the action of proliferation of the follicular epithelial cells of the extract included, as an effective ingredient, in the hair growth phase extender composition of the present invention is derived from one of these ingredients, but as explained above has a strong action of proliferating the follicular epithelial cells overall.

Note that in the hair growth period extender composition of the present invention, a commercially available extract of a plant belonging to the Coriandrum is of course usable.

The amount of the above extract of a plant belonging to the Coriandrum formulated in the hair growth phase extender composition of the present invention may be suitably selected, based upon the specific form of the hair growth phase extender composition of the present invention. It is not particularly limited, but preferably is from 0.00005% by weight to 20.0% by weight, as dried extract, more preferably from 0.01% by weight to 10.0% by weight, based upon the total amount of the composition. When the amount is less than 0.00005% by weight as dried extract, the desired effect of the present invention, that is, the effect of extension of the hair growth phase based on the action of proliferation of the follicular epithelial cells, is not sufficiently exhibited, and therefore, is not preferable. Even if the amount is more than 20.0% by weight, not only can no increase in effect commensurate with the increase in the amount be expected, but also there is a remarkable trend toward causing problems in the preparation of the composition.

In this way, the hair growth phase extender composition according to the present invention containing the above extract of a plant belonging to the Coriandrum as an effective ingredient has an effect of extending the hair growth phase, based on the superior action of proliferating the follicular epithelial cells. As explained above, for example, the hair growth phase extender composition according to the present invention is an agent particularly effective against alopecia derived from the facts that the proliferation of follicular epithelial cells near the hair roots is slow, whereby the shorter growth phase becomes shorter, and the proportion of the quiescent phase hair ending up becoming relatively greater than the growth phase hair. Further, by combining and using hair tonics having other individual effects, it is possible to raise the synergistic effect in specific alopecia.

The means for specifying the action in maintaining or extending the growth phase in a hair cycle, the inherent action in the desired effect of the hair growth phase extender composition of the present invention, that is, the effect of extending the hair growth phase, is not particularly limited so long as the specific method itself is suitable for specifying the action. For example, a specified in vitro method or a specified in vivo method may be used, but considering the convenience and effectiveness, it is preferable to use a specified in vitro method.

Below, one specified in vitro method, that is, the specified method characterized by studying the effect of proliferation of cultured follicular epithelial cells, will be briefly explained (more specifically described in the Examples).

That is, the specified method is the "method of evaluating a hair growth drug comprising bringing a substance into contact with cultured follicular epithelial cells in a keratinocyte growth medium and specifying the presence and/or strength of the cell proliferative activity so as to evaluate the effect of the substance in the extension of the growth phase in the hair cycle and performing secondary screening comprising culturing human follicles in a keratinocyte growth medium containing the substances exhibiting effects by the primary screening so as to further select the substances exhibiting growth of the hair roots", that is, an in vitro method for evaluating hair growth drugs taking note of the follicular epithelial cells, which directly relate to hair growth, and using the cultured cells so as to specify the desired effect of extension of the growth phase in the hair cycle.

In the primary screening of this method of evaluating hair growth drugs, the substance is brought into contact with cultured cells obtained by isolating the follicular epithelial cells of animals (including humans, same below), that is, "cultured follicular epithelial cells" to specify the presence and/or strength of the proliferation.

"Follicular epithelial cells" indicate particularly epithelial cells derived from follicles such as outer root sheath cells or matrix cells. Inside dermal cells are excluded.

The growth phase in the hair cycle is literally the phase where the hair roots grow, that is, where the follicular epithelial cells undergo schizogenesis. The intermediate phase and quiescent phase are phases where these level off and stop.

That is, the substances extending or maintaining the growth phase in the hair cycle are concluded to be substances which maintain the schizogenesis activity of the follicular epithelial cells by administration so as to prevent the transition of the hair to the intermediate phase and quiescent phase of the hair cycle, that is, substances which continue to promote or maintain the proliferation of follicular epithelial cells.

Further, in the secondary screening, human follicles are cultured to further select substances exhibiting growth of hair roots.

At the time of this secondary screening, first, it is necessary to prepare follicle plugs. Usually, it is possible to prepare follicle plugs by selecting hair in the growth phase from among healthy human hair and cutting about the top 2 mm from the hair bulbs of the hair.

If the follicle plugs are cultured by a basal medium containing insulin, the state of the growth phase is maintained for a relatively long time, but if cultured by a basal medium not containing insulin, they change to a state resembling follicles in the intermediate phase in a short period of about one week.

Therefore, when culturing in a basal medium not containing insulin, it is preferable to make the assessment within about one week. When using a medium containing insulin, it becomes possible to extend the culture period to about two weeks. No matter with which medium, it is possible to observe the extent of the growth of the hair roots by culturing the follicles in the presence of the test substance.

Note that the basal medium usable in the secondary screening may be a generally used animal cell culture medium. It is possible to add an antibiotic or an antibacterial to prevent contamination.

The culturing conditions of the follicles may be the normal conditions in animal culture such as 5% $CO_2$ and 37° C. The culture is usually performed for 5 to 14 days.

The growth of the hair roots in the human follicles may for example be visually confirmed in a specimen microscope mounted with a micrometer.

By performing the primary screening and secondary screening in the manner mentioned above, it is possible to specify the action in maintaining or extending the growth phase in the hair cycle or the action in growth of the hair roots.

Note that as an in vitro method of evaluating a hair growth drug, the method of causing the substance to act on the hair papilla cells of an animal and judging the effect of promotion of proliferation may be used.

Further, as a specific in vivo method, the following method is exemplified. That is, the "method of evaluating a hair growth drug comprising administering the substance to a nude mouse, specifying the state of the hair formation portions on the surface of the body of the nude mouse, and evaluating the effect of the substance on extension of the growth phase in the hair cycle", that is, the method of specifying the size of the hair formation portion and speed of movement of the hair formation portion in a nude mouse which in principle is hairless, but characteristically forms hair in a manner where the hair formation portion moves along with time along the body surface so as to evaluate the length of the growth phase in the hair cycle.

The preparation form of the hair growth phase extender composition of the present invention is not particularly limited so long as it is a form capable of applying to the skin. Examples of such forms are a liquid, emulsion, ointment, etc. Further, any type of the hair growth phase extender composition of the present invention is acceptable. For example, a tonic, hair cream, mousse, shampoo, rinse, cream, emulsion, toilet water, pack, or the like can be used.

In addition to the above essential ingredients of the hair growth phase extender composition of the present invention, it is also possible to optionally formulate in, to an extent not impairing the desired effects of the present invention, various oil soluble or water soluble ingredients, humectants, thickeners, preservatives, antioxidants, fragrances, colors, various chemicals, etc. generally used in cosmetics, quasi-drugs, drugs, etc.

For example, oils such as higher saturated fatty acids, solid paraffin, liquid paraffin, silicone oil, squalane, glyceryl monoleate, olive oil, isopropyl myristate, higher alcohols; humectants such as glycerin, hyaluronic acid, propylene glycol, maltitol, atelocollagen, sodium lactate; thickeners such as Malmero (phonetic) sticky substances, carboxyvinyl polymers, xanthane gum; vascular dilators such as nicotinic acid amides, benzyl nicotinate, vitamin E acetate, Swertia herb extract, carpronium chloride, acetyl choline derivatives, amino acids such as serine, methionine, alginin; vitamins such as vitamin $B_6$, vitamin E (or its derivatives), biotin, pantothenic acid (or its derivatives); nicotinic acid esters such as nicotinic acid, methylnicotinic acid, tocopherol nicotinic acid, and skin function promoters such as cepharanthine; female hormones such as estradiol; anti-inflammants such as glycyrrhetinic acid (or its derivatives); antibacterials such as hinokitiol, hexachlorophene, benzalkonium chloride, bithionol; refrigerants such as menthol; organic acids such as salicylic acid, zinc (or its derivatives), lactic acid (or its alkyl esters), etc.; citric acid, etc. may be blended in.

Specific formulations of the hair growth phase extender composition of the present invention will be explained later.

EXAMPLES

The present invention will now be further illustrated by, but is by no means limited to, the following Examples.

Note that in the following Examples, indications of "%" and the internal content mean % by weight unless specifically indicated to the contrary.

First, an explanation will be made of the in vitro cell proliferation test for evaluating the action of extracts of plants used in the examples etc. in extending the hair growth phase.

Test Example 1: Cell Proliferation Test Using Cultured Follicular Epithelial Cells

A. Human Follicular Epithelial Cells
1. Sampling of Human Follicular Epithelial Cells Follicles in the growth phase in the hair cycle were mechanically sampled under a specimen microscope from male human scalps obtained as byproducts of surgery. The follicles in the growth phase were treated by a Delvecco modified MEM (DMEM) containing 1000 U/ml dispase and 0.2% collagenase for 30 minutes at 37° C. Using the front of a syringe needle, the dermal sheaths, dermal papilla, and hair bulb epithelial tissue were removed and the remainder treated by a phosphate buffer containing 0.05% trypsin and 0.02% EDTA [PBS (−)] ((−) means that calcium ions or magnesium ions are not contained) at 37° C. for 5 minutes.

Next, the follicles were allowed to stand in a culture plate coated with collagen (Type I) and external primary culture performed. Note that the medium used at this time was Keratinocyte Growth Medium (KGM) (Keratinocyte Serum Free Medium may also be used).

After 4 to 5 days of culture, the medium was replaced at the point of time when adhesion of the follicles to the culture plate and proliferation of the cells could be confirmed. The medium was then replaced every 3 days thereafter.

The thus proliferated cells were treated with PBS (−) containing 0.05% trypsin and 0.02% EDTA at 37° C. for 5 minutes. The reaction was stopped by an equal amount of 0.1% trypsin inhibitor, then the solution was centrifuged (800×g, 5 minutes) to retrieve the cells.

Next, the cells were made to float in the above keratinocyte growth medium and inoculated in a culture plate coated with collagen (Type I) at a density of 5000 cells/cm$^2$. The medium was replaced every three days until the cells became subconfluent, then were again treated by PBS (−) containing 0.05% trypsin and 0.02% EDTA at 37° C. for 5 minutes. The reaction was then made to stop by an equal amount of 0.1% trypsin inhibitor and the solution centrigued (800×g, 5 minutes). A cell freezing solution (Cell Banker, made by Diatron) was added to the human follicular epithelial cells obtained by this to adjust the concentration to $1.0 \times 10^6$ cells/ml, $1.0 \times 10^6$ cells each were placed in freezing tubes, and these were frozen and stored. Note that the cell count was calculated by a hemocytometer.

2. Assay of Substance to be Tested

The rate of intermixture of fibroblasts in the follicular epithelial cells obtained by the above process (i.e., FB intermixing rate) was measured (3000×, 5 fields). Samples with FB intermixture rates of over 3% as a result were eliminated from the assay.

The follicular epithelial cells were inoculated in a culture flask, then treated by PBS (−) containing 0.25% trypsin and 0.02% EDTA. The reaction was then stopped by a 0.1% trypsin inhibitor, and the system was centrifuged at 1500 rpm for 5 minutes. The supernatent was removed, then 20 ml of KGM medium was added to the residue to prepare a cell suspension.

The cells were inoculated in a 96 well-plate (I-type collagen coated plate, made by Falcon Co.) at a rate of 0.2 ml/well ($3.0 \times 10^3$ cells/well). They were allowed to stand at about 20 minutes at room temperature until the cells sank to the bottom of the wells.

Next, the cells were cultured at 37° C. in 5% $CO_2$ for 1 day to obtain the desired human cultured follicular epithelial cells.

B. Sampling of Rat Follicular Epithelial Cells
1. Sampling of Rat Follicular Epithelial Cells
   (1) Sampling of Follicle Dorsal skin of newborn (3 to 4 day old) rats was immersed in PBS (−) containing 5% PSF, then the underlying subcutaneous fat and membrane were removed from the skin fat layer by dissection scissors. Next, the dorsal skin was again immersed in PBS (−) containing 1% PSF, then was soaked overnight in PBS (−) containing 0.25% trypsin and 0.02% EDTA (the same hereinbelow) at 4° C.

After immersion in the trypsin solution, the dermis layer and the epidermis layer of the dorsal skin were peeled off by tweezers, then the dermis layer was cut by scissors in Ham's F12 medium containing 0.35% collagenase [composition (mg/L): 1-Alanin (8.9), 1-Arginine (HCl:211), 1-Asparagine (13.2), 1-Asparatic acid (13.3), 1-Cysteine (HCl:31.5), 1-Glutamic acid (14.7), 1-Glutamine (146), Glycine (7.5), 1-Histidine (HCl:19), 1-Isoleucine (3.9), 1-Leucine (13.1), 1-Lysine (HCl:36.5), 1-Methionine (4.5), 1-Phenylalanin (5.0), Proline (34.5), 1-Serine (10.5), 1-Threonine (11.9), 1-Tryptophane (2.0), 1-Tyrosine (5.4), 1-Valine (11.7), Biotine (0.0073), Choline (Cl:14.0), Vitamin B12 (1.36), Folic acid (1.32), Inositol (18.0), Nicotinamide (0.037), Pantothenic acid (Ca:0.477), Vitamin B6 (HCl:0.062), Vitamin B2 (0.038), Vitamin B1 (HCl: 0.337), $CaCl_2$ ($2H_2O{:}_{44.0}$), $CuSO_4 \cdot 5H_2O$ (0.0025), $FeSO_4 \cdot 7H_2O$ (0.834), KCl (224.0), $MgCl_2$ ($6H_2O$: 122), "Proc. Natl. Acad. Sci. USA, 53, 288 (1965)" hereinafter the same]. The medium containing these cut pieces was then soaked at 37° C. for 35 minutes (60 rpm). After the soaking, pipetting was performed until clumps could no longer be seen in the collagenase reaction product, Ham's F12 medium containing DNase (10,000 units) was added, and the mixture was allowed to stand for 5 minutes.

After being allowed to stand, the suspension obtained was further pipetted, then was filtered by a nylon mesh (Nytex 157 mesh).

The suspension was diluted by PBS (−), then the diluted solution was centrifuged (4° C., 400 rpm, 5 minutes). After centrifugation, the supernatant was removed and the fat portion was removed from the system.

Next, PBS (−) was added to the residue to make a suspension, then this was further centrifuged [(4° C., 400 rpm, 5 minutes)×3 times].

The residue obtained by this centrifugation operation was the follicles in the dorsal skin of the rats.

(2) Sampling of Follicular Epithelial Cells 5 ml of PBS (−) containing 0.25% trypsin and 0.02% EDTA was added to the follicles obtained by the above operation. The cell suspension was incubated at 37° C. for 5 minutes.

After the incubation, equal amounts of 0.1% trypsin inhibitor and Ham's F12 medium were added, the cell suspension was filtered by a cell strainer (100 µm, made by Nalgene Co.), then the cell suspension was centrifuged (4° C., 1500 rpm, 5 minutes). The supernatant was removed from the system to obtain, as a residue, the desired follicular epithelial cells. A cell freezing solution (Cell Banker, made by Diatron) was added to the follicular epithelial cells to adjust the concentration to $1.5 \times 10^7$ cells/ml, $1.5 \times 10^7$ cells each were added to freezing tubes, and these were frozen and stored. The number of cells was calculated with a blood count plate.

2. Preculture of Follicular Epithelial Cells

The fibroblasts mixed in the system were removed from the system as much as possible, then the follicular epithelial cells obtained from the above process were precultured. This procedure will be explained below.

The frozen cells obtained by the above process were thawed in a 37° C. incubator. Next, a FAD medium [Ham's F12 medium (explained later) and MEN medium mixed in a 3 to 1 volume ratio to which was added a medium containing insulin (5.0 µg/ml), hydrocortizone (0.45 µg/ml), epidermal growth factor (EGF) (10.0 ng/ml), cholera toxin ($10^{-9}$ M), and fetal bovine serum (10%), same below] was added to dilute the cell solution. The system was then centrifuged (not more than 10° C., 1500 rpm, 5 minutes). After centrifugation, the supernatant was removed, FAD medium was added to the system, and pipetting was repeated until cell clumps could no longer be observed.

Next, samples were prepared using the FAD medium to give a cell concentration of $2.5 \times 10^5$ cells/ml.

Cells were inoculated in a 75 $cm^3$ culture flask coated with I-type collagen and were cultured at 37° C. in 5% $CO_2$ overnight.

After the culture, the system was washed by PBS (−), PBS (−) containing 0.25% trypsin and 0.02% EDTA was added, and this was incubated at 37° C. in 5% $CO_2$ for 4 minutes. An equal amount of 0.1% trysin inhibitor as the trypsin solution was added to the system, rinsing was performed once lightly, the supernatent was removed, and the fibroblasts mixed in the system were removed.

Further, a KGM medium [Keratinocyto growth medium: comprised of Keratinocyto basal medium (KBM medium (modified MCDB153 medium (made by Chronetics Co.)) plus added bovine pituitary extract (BPE) (0.4 vol %), insulin (0.5 µm/ml), hydrocortizone (0.5 µm/ml), h-EGF (0.1 ng/ml), hereinafter the same] was added and the result cultured at 37° C. in 5% $CO_2$ for 3 days.

3. Assay of Substance

The rate of intermixture of fibroblasts in the culture flask inoculated with the follicular epithelial cells obtained by the above process (FB intermixture rate) was measured (3000×, 5 visual fields). Samples with FB intermixture rates of over 2% as a result were eliminated from the assay.

The system was washed with PBS (−), PBS (−) containing 0.25% trypsin and 0.02% EDTA was added, and the result was incubated at 37° C. for 3 minutes. Next, the difference in reactivity of the epithelial cells and the fibroblasts with trypsin was used to remove the fibroblasts from the system by removing the trypsin, then again PBS (−) containing 0.25% trypsin and 0.02% EDTA was added and the result shaken at 37° C. at 20 rpm for 5 minutes.

Next, peeling of cells was confirmed under a microscope, then DMEM medium containing 10% FBS was added and pipetted. The system was centrifuged at 1500 rpm for 5 minutes.

The supernatant was removed, KGM medium added, then pipetting performed until there were no longer any clumps of cells.

The suspension was filtered by a cell strainer (100 µm, made by Nalgene Co.), then the number of live cells in the suspension was calculated by a hemocytometer. KGM medium was added to the system to adjust the cell concentration in the system to $2.0 \times 10^4$ cells/ml.

Next, a 96 well-plate (I-type collagen coated plate: made by Falcon Co.) was inoculated ($4.0 \times 10$ cells/well) at a rate of 0.2 ml/well. It was then allowed to stand for approximately 20 minutes at room temperature until the cells sank to the bottoms of the wells.

Next, it was incubated at 37° C. in 5% $CO_2$ for 1 day to obtain the desired human cultured follicular epithelial cells.

C. Preparation of Test Media for First Aspect of Present Invention (1) Preparation of Substance Media The substances were added to the KBM medium at the concentration of 1.0 µmol/liter with respect to the medium with 0.1% DMSO.

(2) Preparation of Control Medium

Negative control: Prepared by adding DMSO (solvent) to the KBM medium to give a final concentration of 0.1%.

Positive control: Prepared by adding final concentrations of 5 µg/ml of insulin and 0.5 µg/ml of hydrocortizone to the negative control medium.

C'. Preparation of Test Media for Second Aspect of Present Invention (1) Preparation of Extract 500 g of commercially available coriander (dried) was immersed in 10 liters of 70% methanol at room temperature (23° C.) for 24 hours two times. The solvent was distilled off from the extract to obtain 57.5 g of a dried 70% methanol extract of coriander.

(2) Preparation of Substance Media

About 1.5 mg of the above coriander extract was weighted in a screw tube and diluted to a 0.2% solution by an organic solvent (DMSO).

Similarly, as controls, 0.2% DMSO solutions of tea extract (extraction method: water extraction) and Ophiopogon tuber extract (extraction method: 10% ethanol extraction) were prepared.

Next, the DMSO solutions of the above herbal extracts were added to 1000 times the volume of the above KBM medium (extract concentration: $2.0 \times 10^{-4}$% (DMSO 0.1%)).

0.2 ml amounts of these substance media were added to 1.8 ml amounts of KBM medium containing 0.1% DMSO to adjust the concentrations of the substances to $2.0 \times 10^{-5}$% (10 fold dilution).

(3) Preparation of Control Medium

Negative control: Prepared by adding 2 µl of DMSO (solvent) to 2 ml of KBM medium (DMSO 0.1%).

Positive control: Prepared by adding 2 µl of insulin (5 mg/ml) and 2 µl of hydrocortizone (0.5 mg/ml) to the negative control medium.

D. Exchange of Substance Media

In the above A and B, the KGM media in the 96 well-plates prepared with the human cultured follicular epithelial cells and rat cultured follicular epithelial cells were exchanged with the substance media and control medium (200 µl/well). After exchange, they were cultured at 37° C. in 5% $CO_2$ for 2 days.

Note that the media were exchanged by withdrawing the KGM media in the wells by a multipipette while taking care not to damage the cells adhered to the bottom and then quickly adding the substance media etc. from the two ends of the wells.

E. Measurement of Cell Proliferation

Alamar blue (made by Alamar Bioscience Co.) was added in an amount of 1/10 the amount of the medium (by volume) and incubated at 37° C. (5% $CO_2$) for 6 hours.

After incubation, the absorbances at 595 nm and 570 nm of the system were measured using a microplate reader (made by Bio RAD Co.) The cell proliferation degree was calculated in accordance with the following equation:

Method of calculation of cell proliferation degree (Cell proliferation degree of sample)=(alamar blue reduction rate of sample)/(alamar blue reduction rate of negative control)×100 (%)

Further, the cell proliferation promotion indicator was calculated by the following equation:

(Cell proliferation promotion indicator of sample)

[(Cell proliferation degree of sample)-(Cell proliferation degree of negative control)]/[(Cell proliferation degree of positive control)-(Cell proliferation degree of negative control)]

At this time, the cell proliferation promotion indicator of the negative control becomes 0 and the cell proliferation promotion indicator of the positive control becomes 1.

F. Results for First Aspect of Present Invention (1) The above cell proliferation promotion indicator in the above substance for the first aspect of the present invention measured is shown in the following Table 1.

TABLE 1

| Fatty acid | Follicular epithelial cell proliferation promotion indicator | |
|---|---|---|
| | Rat-derived cells | Human-derived cells |
| Palmitoleic acid | 0.7 | 0.6 |
| Petroselinic acid | 1.2 | 1.2 |
| Oleic acid | 1.5 | 1.3 |
| Linolic acid | 1.1 | 1.0 |
| α-linoleic acid | 1.1 | 1.0 |
| γ-linoleic acid | 1.1 | 1.0 |
| Arachidonic acid | 1.3 | 1.2 |
| Decosahexaenoic acid | 1.2 | 1.1 |

From these results, the proliferative activity of cultured follicular epithelial cells was reliably observed in the above unsaturated fatty acids. That is, it became clear that an action in maintaining and extending the growth phase of hair was observed through maintaining the schizogenesis activity of follicular epithelial cells in the above unsaturated fatty acids.

G. Studies on Growth of Hair Roots (Secondary Screening)

Further, we studied the effect of hair growth in the above unsaturated fatty acids.

Organ Culture of Human Follicles

Using a microscalpel under a specimen microscope, follicles in the growth phase were isolated from the human scalp. The isolated follicles were washed by a "Williams E medium (Gibco) in which penicillin, streptomycin, and fungizone had been added" (hereinafter referred to as the (−) medium), then measured for length. These were immersed in the (−) medium to which were further added 10 ng/ml of hydrocortisone, 10 µg/ml of insulin, 10 ng/ml of sodium selenite, and 10 µg/ml of transferin (hereinafter also referred to as the (+) medium) (24-well microplate used: 1 ml per well) and cultured overnight in 5% $CO_2$ at 37° C. (preculture). The lengths of the follicles cultured again after the preculture were measured, the follicles with growth of over 0.25 mm were selected, and the follicles were divided into three groups of nine each to give a uniform extent of growth.

The lengths of the hair roots in the follicles were measured by examining the above microplate visually using a microscope equipped with a micrometer.

Assessment of Substances

DMSO solutions of the substances were added to (−) media to give a final concentration of the substances, that is, the above unsaturated fatty acids, of 10 µmol/liter (DMSO 0.1%).

Further, a medium (control medium) was prepared by adding an organic solvent (DMSO) to the (−) medium simultaneously to give a final concentration of 0.1%.

Media of the above three follicle groups were replaced with the above media and cultured for a further 5 days under 5% $CO_2$ at 37° C. The lengths of the follicles on day 5 after the start of culture were measured. The lengths of the hair roots in follicles were compared between the control group and the substance groups.

The results are shown in Table 2.

TABLE 2

| Fatty acid | Growth of hair roots (mm) Human follicles (organ culture) |
|---|---|
| Palmitoleic acid | 1.4 |
| Petroselinic acid | 1.6 |
| Oleic acid | 1.8 |
| Linolic acid | 1.5 |
| α-linoleic acid | 1.5 |
| γ-linoleic acid | 1.5 |
| Arachidonic acid | 1.6 |
| Decosahexaenoic acid | 1.6 |
| Control | 1.2 |

From these results, it has become clear that not only do unsaturated fatty acids promote the proliferation of follicular epithelial cells, but they also are observed to have the effect of promoting the growth of hair roots in follicles and extending the growth phase hair in a balanced fashion as a follicular organ.

H. Results for Second Aspect of Present Invention

The cell proliferation degree of the coriander extract determined above was 0.5 in human-derived cultured follicular epithelial cells and 0.5 in rat-derived cultured follicular epithelial cells as well.

From these results, it was found that a proliferative activity of cultured follicular epithelial cells was clearly observed in the extract of coriander, that is, an extract of a plant belonging to the Coriandrum.

That is, it became clear that an activity in extending the growth phase of hair was observed in an extract of a plant belonging to the Coriandrum.

The formulations of the hair growth phase extender composition according to the first aspect of the present invention will now be shown as Examples. The results of the hair growth were studied.

Example I-1: Preparation of Liquid Hair Growth Phase Extender Composition 0.1% petroselinic acid and 0.1% oleic acid were stirred, mixed, and dissolved in 90% 70% ethanol, 0.49% dodecylbenzene sulfonate, 0.5% hydrogenated castor oil ethylene oxide (40 moles) adduct, and ion exchanged water (balance). Ion exchanged water (10%) was added and mixed with this to obtain a liquid hair growth phase extender composition.

In the formulation of the liquid hair growth phase extender composition, the petroselinic acid and oleic acid were omitted to prepare a liquid agent which was used as a control (Comparative Example I-1).

Example I-2: Preparation of Emulsion Type Hair Growth Phase Extender Composition An emulsion type hair growth phase extender composition was prepared by the following formula:

| Ingredient of formulation | Amount (wt %) |
|---|---|
| (Phase A) | |
| Petroselinic acid | 1.0 |
| Polyoxyethylene (60 moles) added hydrogenated castor oil | 2.0 |
| Glycerin | 10.0 |
| Dipropylene glycol | 10.0 |
| 1,3-butylene glycol | 5.0 |
| Polyethylene glycol 1500 | 5.0 |
| (Phase B) | |
| Cetyl isooctanate | 10.0 |
| Squalane | 5.0 |
| Vaseline | 2.0 |
| Propyl paraben | 2.0 |
| (Phase C) | |
| 1% aqueous solution of carboxyvinyl polymer | 30.0 |
| Sodium hexametaphosphate | 0.03 |
| Ion exchanged water | 8.35 |
| (Phase D) | |
| Ion exchanged water | 4.5 |
| (Phase E) | |
| KOH | 0.12 |
| Ion exchanged water | 5.0 |

<Production Method>

The phase A and phase B were heated, melted, and mixed at 60° C. and processed by a homomixer to produce a gel. The phase D was gradually added to this and dispersed by a homomixer.

Next, the melted phase C was added to this, the finally melted phase E was added, and the mixture emulsified by a homomixer to obtain an O/W emulsion type hair growth phase extender composition.

Example I-3: Preparation of Cream-Like Hair Growth Phase Extender Composition

A cream-like hair growth phase extender composition was prepared by the following formula:

| Ingredient of formulation | Amount (wt %) |
|---|---|
| (Phase A) | |
| Liquid paraffin | 5.0 |
| Cetostearyl alcohol | 5.5 |
| Glyceryl monostearate | 3.0 |
| EO (20 mole)-2-octyldodecyl ether | 8.0 |
| Propyl paraben | 0.3 |
| Fragrance | 0.1 |
| (Phase B) | |
| Petroselinic acid | 5.0 |
| Glycerin | 8.0 |
| Dipropylene glycol | 20.0 |
| Polyethylene glycol 4000 | 5.0 |
| Sodium dodecyl sulfate | 0.1 |
| Sodium hexametaphosphate | 0.005 |
| Ion exchanged water | 39.995 |

<Production Method>

The phase A and phase B were heated, melted, and mixed, then emulsified by a homomixer to obtain a cream-like hair growth phase extender composition.

Example I-4: Study of Hair Growth Action of Hair Growth Phase Extender Composition of Present Invention To investigate the prevention of hair loss, the hair formation effect, and other hair growth actions of the hair growth phase extender composition of the present invention, a tricogram test was performed on humans by the following method. The test samples and control sample were the hair growth phase extender compositions of the present invention of Examples I-1 to I-3, the composition of Comparative Example I-1, and 70% ethanol.

Test Method

Hair roots of removed hair before use of the above sample and after use were examined under a microscope. The number of hair roots of hair which had stopped growing, that is, "hair roots in the quiescent phase" (people who claim hair loss are deemed to have a greater proportion of hair roots in the quiescent phase compared with normal people) were counted. The change in the proportion was used to compare the hair growth action of the samples.

That is, the test samples and control sample were coated on the scalps of 10 male test subjects twice a day in 2 ml amounts each per time continuously for six months. Right before coating and right after the end of the coatings in the six month period, 100 hairs were removed per test subject. The hair roots were examined under a microscope. Further, practical tests were performed on the validity or invalidity of the hair growth effect in the samples.

The results of these tests are shown in the following Table 3.

TABLE 3

| Sample | Proportion of hair roots in quiescent phase | | | Assessment |
|---|---|---|---|---|
| (Control and hair growth promoter no.) | Over 20% reduction (%) | ±20% (%) | Over 20% increase (%) | of hair growth effect |
| Control (70% ethanol) | 10 | 50 | 40 | Invalid |
| Ex. I-1 | 55 | 20 | 25 | Valid |
| Ex. I-2 | 50 | 35 | 15 | Valid |
| Ex. I-3 | 60 | 25 | 15 | Valid |
| Comp. Ex. I-1 | 10 | 55 | 35 | Invalid |

From the results of Table 3, a hair growth effect based on the effect of extending the hair growth phase of petroselinic acid was observed in the hair growth phase extender composition of the present invention formulated having an unsaturated fatty acid, that is, petroselinic acid, as an effective ingredient.

Further, a similar effect of extending the hair growth phase as in petroselinic acid was observed in unsaturated fatty acids other than the above petroselinic acid, so it is clear that a hair growth effect is similarly observed as in the above embodiment in a hair growth phase extender formulated having these vegetable oil extracts etc. as effective ingredients.

According to the first aspect of the present invention, a hair growth phase extender composition which maintains or extends the growth phase in the hair cycle by promoting hair growth can be provided as shown above.

The formulations of the hair growth phase extender composition according to the second aspect of the present invention will be shown as Examples. The results of the hair growth were studied.

Example II-1: Preparation of Liquid Hair Growth Phase Extender Composition 0.1% of a dried 70% methanol extract of coriander was mixed, stirred, and dissolved in 90% 70% ethanol, 0.1% sodium oleate, 0.49% dodecylbenzene sulfonate, 0.5% hydrogenated castor oil ethylene oxide (40 moles) adduct, and ion exchanged water (balance). Ion exchanged water (10%) was added and mixed with this to obtain a liquid hair growth phase extender.

In the formulation of the liquid hair growth phase extender composition, 0.1% of a dried 10% ethanol extract of Ophiopogon tuber was added, instead of the 70% methanol extract of coriander, to prepare a liquid agent as a control (Comparative Example II-1).

Example II-2: Preparation of Emulsion Type Hair Growth Phase Extender Composition In the above process of production of a coriander extract, ethanol was used instead of the 70% methanol to obtain an extract. This was used as an emulsion type hair growth phase extender composition of the following formulation.

| Ingredient of formulation | Amount (wt %) |
|---|---|
| (Phase A) | |
| Coriander extract, dried | 1.0 |
| Polyoxyethylene (60 moles) added hydrogenated castor oil | 2.0 |
| Glycerin | 10.0 |
| Dipropyl glycol | 10.0 |
| 1,3-butylene glycol | 5.0 |
| Polyethylene glycol 1500 | 5.0 |
| (Phase B) | |
| Cetyl isooctanate | 10.0 |
| Squalane | 5.0 |
| Vaseline | 2.0 |
| Propyl paraben | 2.0 |
| (Phase C) | |
| 1% aqueous solution of carboxyvinyl polymer | 30.0 |
| Sodium hexametaphosphate | 0.03 |
| Ion exchanged water | 8.35 |
| (Phase D) | |
| Ion exchanged water | 4.5 |
| (Phase E) | |
| KOH | 0.12 |
| Ion exchanged water | 5.0 |

<Production Method>

The phase A and phase B were heated, melted, and mixed at 60° C. and processed by a homomixer to produce a gel. The phase D was gradually added to this and dispersed by a homomixer.

Next, the melted phase C was added to this, the finally melted phase E was added, and the mixture emulsified by a homomixer to obtain an O/W emulsion type hair growth phase extender composition.

Example II-3: Preparation of Cream-Like Hair Growth Phase Extender Composition

In the same way as Example II-2, a dried ethanol extract of coriander was used in a cream-like hair growth phase extender composition of the following formula:

| Ingredient of formulation | Amount (wt %) |
|---|---|
| (Phase A) | |
| Liquid paraffin | 5.0 |
| Cetostearyl alcohol | 5.5 |

-continued

| Ingredient of formulation | Amount (wt %) |
|---|---|
| Glyceryl monostearate | 3.0 |
| EO (20 mole)-2-octyldodecyl ether | 8.0 |
| Propyl paraben | 0.3 |
| Fragrance | 0.1 |
| (Phase B) | |
| Coriander extract, dried | 5.0 |
| Glycerin | 8.0 |
| Dipropyl glycol | 20.0 |
| Polyethylene glycol 4000 | 5.0 |
| Sodium dodecyl sulfate | 0.1 |
| Sodium hexametaphosphate | 0.005 |
| Ion exchanged water | 39.995 |

<Production Method>

The phase A and phase B were heated, melted, and mixed, then emulsified by a homomixer to obtain a cream-like hair growth phase extender composition.

Example II-4: Study of Hair Growth Action of Hair Growth Phase Extender Composition of Present Invention To investigate the prevention of hair loss, the hair formation effect, and other hair growth actions of the hair growth phase extender composition of the present invention, a tricogram test was performed on humans by the following method. The test samples and control sample were the hair growth phase extender compositions of the present invention of Examples II-1 to II-3, the composition of Comparative Example II-1, and 70% ethanol.

Test Method

Hair roots of removed hair before use of the above sample and after use were examined under a microscope. The number of hair roots of hair which had stopped growing, that is, "hair roots in the quiescent phase" were counted. The change in the proportion was used to compare the hair growth action of the samples.

That is, the test samples and control sample were coated on the scalps of 10 male test subjects twice a day in 2 ml amounts each per time continuously for six months. Right before coating and right after the end of the coatings in the six month period, 100 hairs were removed per test subject. The hair roots were examined under a microscope. Further, practical tests were performed on the validity or invalidity of the hair growth effect in the samples.

The results of these tests are shown in the following Table 4.

TABLE 4

| Sample | Proportion of hair roots in quiescent phase | | | Assessment |
|---|---|---|---|---|
| (Control and hair growth promoter no.) | Over 20% reduction (%) | ±20% (%) | Over 20% increase (%) | of hair growth effect |
| Control (70% ethanol) | 10 | 50 | 40 | Invalid |
| Ex. II-1 | 45 | 30 | 25 | Valid |
| Ex. II-2 | 45 | 40 | 15 | Valid |
| Ex. II-3 | 50 | 30 | 10 | Valid |
| Comp. Ex. II-1 | 10 | 55 | 35 | Invalid |

From the results of Table 4, a hair growth effect based on the effect of extending the hair growth phase of the effective ingredient was observed in the hair growth phase extender composition of the present invention.

As explained above, according to the second aspect of the present invention, a hair growth phase extender composition which extends the growth phase in the hair cycle by activating the proliferation of follicular epithelial cells can be provided.

What is claimed is:

1. A hair growth phase extender composition for a subject in need thereof, comprising an extract of a fruit of coriander as an effective ingredient in an amount of 500 ppb to 20.0% by weight, and a pharmaceutically effective carrier thereof, wherein said extract is extracted with a solvent selected from the group consisting of lower alcohols and lower polyols.

2. A method of preparing a hair growth phase extender composition of claim 1, comprising:

optionally drying or pulverizing a fruit of coriander belonging to the Coriandrum; and extracting said fruit with an extraction solvent to provide an extract of said fruit; and mixing said extract with a pharmaceutically effective carrier of said extract to provide a hair growth phase extender composition.

3. A method of preparing a hair growth phase extender composition of claim 2, wherein said solvent is selected from the group consisting of lower alcohols and lower polyols.

4. A method of preparing a hair growth phase extender composition of claim 2 further comprising the step of:

distilling off said extraction solvent before mixing said extract with said pharmaceutically effective carrier.

* * * * *